United States Patent
Steffier

(10) Patent No.: US 8,574,558 B2
(45) Date of Patent: Nov. 5, 2013

(54) UV-CURABLE NAIL COATING FORMULATIONS BASED ON RENEWABLE POLYOLS

(75) Inventor: Lawrence W. Steffier, Cherry Hill, NJ (US)

(73) Assignee: Mycone Dental Supply Co., Inc., Cherry Hill, NJ (US)

( * ) Notice: Subject to any disclaimer, the term of this patent is extended or adjusted under 35 U.S.C. 154(b) by 317 days.

(21) Appl. No.: 13/012,066

(22) Filed: Jan. 24, 2011

(65) Prior Publication Data

US 2011/0182837 A1 Jul. 28, 2011

Related U.S. Application Data

(60) Provisional application No. 61/298,015, filed on Jan. 25, 2010.

(51) Int. Cl.
*A61K 8/00* (2006.01)
*A61K 9/00* (2006.01)
*A61K 31/74* (2006.01)

(52) U.S. Cl.
USPC .......... 424/61; 424/400; 424/401; 424/78.02; 424/78.08; 424/78.31

(58) Field of Classification Search
USPC ........... 424/61, 400, 401, 78.02, 78.08, 78.31
See application file for complete search history.

(56) References Cited

U.S. PATENT DOCUMENTS

| | | | | |
|---|---|---|---|---|
| 5,985,951 A | * | 11/1999 | Cook | 522/88 |
| 6,054,251 A | * | 4/2000 | Imai et al. | 430/285.1 |
| 6,153,356 A | * | 11/2000 | Urano et al. | 430/281.1 |
| 6,420,090 B1 | * | 7/2002 | Kojima et al. | 430/284.1 |

OTHER PUBLICATIONS

Wermuth, Drug Discovery Today, 2006, 11 (7/8), 348-354.*
The Merriam-Webster Online Dictionary, obtained online at: http://www.merriam-webster.com/dictioanry/analogue, downloaded on Jul. 5, 2008.*

* cited by examiner

*Primary Examiner* — Abigail Fisher
(74) *Attorney, Agent, or Firm* — Michael B. Fein, Esq.; Eckert Seamans Cherin & Mellott, LLC

(57) ABSTRACT

A photopolymerizable composition for forming a cosmetic coating for natural and artificial nails of humans and animals comprising a photoinitiator and a (meth)acrylate monomer prepared by reacting a core polyol derived or functionalized from a renewable resource with an a (meth)acrylate monomer and coatings formed from such compositions under UV or other radiation.

11 Claims, No Drawings

UV-CURABLE NAIL COATING FORMULATIONS BASED ON RENEWABLE POLYOLS

BACKGROUND OF THE INVENTION

This invention relates to compositions for photopolymerizable coatings forming cosmetic films that are especially useful for human and animal nail coatings. Such compositions are capable of free radical addition or cation cure reactions with unsaturated ethylenic pendant groups on compounds upon exposure to actinic radiation in the presence of a photoinitiator.

Ultra-violet radiation (UV) is the most conventional form of actinic radiation used to cure gels in this art, however, visible light curing systems are also known. Professional nail technicians most typically apply UV curable gels designed for sculpting nails. Such UV-curable gels are usually composed of acrylic or methacrylic monomers and oligomers in a gel-like state that requires curing under a UV lamp. Such nail finishes can be applied directly to natural fingernails or toenails, or alternatively can be applied to nail extensions bonded to fingernails. In many cases, the artificial nails are coated with conventional nail polish after they are cured.

There has been a strong movement to design environmentally friendly chemical compositions. In the field of nail polishes and nail coating compositions, there have been no commercially available compositions which are marketed as being environmentally friendly.

It is an object of this invention to provide a nail coating composition which has properties which are either comparable to or superior to existing commercial radiation curable nail coating compositions.

SUMMARY OF THE INVENTION

These objects and others which will become apparent from the following disclosure are achieved by the present invention which comprises in one aspect a photopolymerizable composition for forming a cosmetic coating for natural and artificial nails of humans and animals, the composition comprising a photoinitiator and a (meth)acrylate monomer and/or oligomer prepared by reacting a core polyol with a (meth)acrylate monomer and optionally one or more co-reactants selected from the group consisting of an organic diisocyanate, a polyacid, polyester, cyclic lactone, cyclic lactam, ethylene oxide, propylene oxide, epoxy compounds, polyols, and polyamines wherein the core polyol is derived from a renewable resource. In some embodiments the (meth)acrylate monomer has one polyol unit and the (meth)acrylate oligomer has multiple polyol units. The term "(meth)acrylate" includes both acrylates and methacrylates. As is customary in this radiation curable nail coating art, the composition may include one or more optional additives. The optional additives can be monomers, polymers, oligomers, crosslinkers, pigments, colorants, dyes, UV-absorbing or reflecting materials, micas, glitters, flavors, fragrances, thixotropic additives, dispersants and/or any other additives known in the art of radiation curable nail coatings.

The monomers containing and reactive oligomers are prepared by reacting a core polyol with a (meth)acrylate monomer and optionally one or more co-reactants selected from the group consisting of an organic diisocyanate, a polyacid, polyester, cyclic lactone, cyclic lactam, ethylene oxide, propylene oxide, epoxy compounds, polyols, and polyamines, wherein the core polyol is derived from a renewable resource are novel in radiation curable nail coating compositions. Preferably, the core polyol is a naturally occurring and/or renewable compound which contains pendant reactive hydroxyl groups.

When applied to human or artificial nails, the compositions cure under UV radiation or natural light and form a hard and solvent resistant coating which adheres to the nail. The compositions can optionally be designed to be removed with solvent. The core polyol can contribute to improved application performance, adhesion, wear, and/or durability of photopolymerized nail coatings.

The compositions, methods of use, and resultant artificial nails or cured coatings are also aspects of this invention.

DETAILED DESCRIPTION

The photopolymerizable compositions of the invention form a cosmetic coating for natural and artificial nails of humans and animals. The compositions comprise one or more photopolymerizable (meth)acrylate monomers and/or oligomers prepared by reacting a core polyol with a (meth)acrylate monomer and optionally one or more co-reactants selected from the group consisting of an organic diisocyanate, a polyacid, polyester, cyclic lactone, cyclic lactam, ethylene oxide, propylene oxide, epoxy compounds, polyols, and polyamines, wherein the core polyol is derived from a renewable resource. These photopolymerizable monomers and/or oligomers can in some embodiments comprise an ethylenically-unsaturated crosslinking reagent. Such crosslinking reagent can be a (meth)acrylate monomer or any other ethylenically unsaturated monomer. In some embodiments the (meth)acrylate monomer has one polyol unit and the (meth)acrylate oligomer has multiple polyol units.

In addition to the above-described (meth)acrylate-based polymerizable monomers, other polymerizable monomers, oligomers or polymers of monomers which contain at least one free radical polymerizable group in the molecule may be used. These monomers may contain other groups such as carboxyl groups to improve adhesion. Examples of optional monomers are esters and amides of acrylic and methacrylic acid. The esters of acrylic and methacrylic acid are herein termed (meth)acrylic ester. Specific but not limiting examples of mono methyl (meth)acrylic esters include: methyl (meth)acrylate, ethyl (meth)acrylate hydroxypropyl (meth)acrylate, ethyl (meth)acrylate, butyl (meth)acrylate, hydroxy ethyl (meth)acrylate, butoxyethyl (meth)acrylate, diethylaminoethyl (meth)acrylate, 2-ethylhexyl (meth)acrylate, ethoxyethyl (meth)acrylate, t-butyl aminoethyl (meth)acrylate, methoxyethylene glycol (meth)acrylate, phosphoethyl (meth)acrylate, methoxy propyl (meth)acrylate, methoxy polyethylene glycol(meth)acrylate, phenoxyethylene glycol (meth)acrylate, phenoxypolyethylene glycol (meth)acrylate, 2-hydroxy-3-phenoxypropyl (meth)acrylate, 2-(meth)acryloxyethylsuccinic acid, 2-(meth)acryloylethylphthalic acid, 2-(meth)acryloyloxypropylphthalic acid, stearyl (meth)acrylate, isobornyl (meth)acrylate, 3-chloro-2-hydroxypropyl (meth)acrylate, tetrahydrofurfuryl (meth)acrylate, (meth)acrylamides and allyl monomers.

Optional oligomers include urethane(meth)acrylates having at least two or more acryl or methacryl groups and a urethane group. Examples include: urethanes based on aliphatic, aromatic, polyester, and polyether polyols and aliphatic, aromatic, polyester, and polyether diisocyanates capped with (meth)acrylate end-groups. Isocyanate prepolymers can also be used in place of the polyol-diisocyanate core.

Other oligomers include epoxy (meth)acrylates and epoxy urethane (meth)acrylates having at least two or more acryl or methacryl groups and, optionally, a urethane group. Examples include epoxy (meth)acrylates based on aliphatic or aromatic epoxy prepolymers capped with (meth)acrylate end-groups. An aliphatic or aromatic urethane spacer can be optionally inserted between the epoxy and the (meth)acrylate endgroup(s). Other oligomers include acrylated polyester oligomers having at least two or more acryl or methacryl groups and a polyester core. Acrylated polyether oligomers having at least two or more acryl or methacryl groups and a polyether core are also optional. Acrylated acrylate oligomers having at least two or more acryl or methacryl groups and a polyacrylic core can be used in some embodiments.

These reactive urethanes, epoxies, polyesters, polyethers and acrylics are available from several suppliers including BASF Corporation, Bayer MaterialScience, Bomar Specialties Co, Cognis Corporation, Cytec Industries Inc, DSM NeoResins, Eternal Chemical Co, Ltd, IGM Resins, Rahn AG, Sartomer USA, LLC, Double Bond Chemical, Miwon and SI Group, Inc.

Examples of crosslinkers are difunctional methacryl esters such as 1,4-butane diol di(meth)acrylate, 1,6-hexanediol di(meth)acrylate, 1,9-nonanediol di(meth)acrylate, 1,10-decanediol di(meth)acrylate, neopentyl glycol di(meth)acrylate, 2-methyl-1,8-octane diol di(meth)acrylate, glycerol di(meth)acrylate, ethylene glycol di(meth)acrylate, triethylene glycol di(meth)acrylate, polyethylene glycol di(meth)acrylate, polypropylene glycol di(meth)acrylate, ethoxylated propylene glycol di(meth)acrylate, ethoxylated polypropylene glycol di(meth)acrylate, polyethoxypropoxy di(meth)acrylate, ethoxylated bisphenol A di(meth)acrylate, propoxylated bisphenol A di(meth)acrylate, propoxylated ethoxylated bisphenol A di(meth)acrylate, bisphenol-A glycidyl methacrylate, tricyclodecanedimethanol di(meth)acrylates glycerin di(meth)acrylate, ethoxylated glycerin di(meth)acrylate, bis acrylamides, bis allyl ethers and allyl (meth)acrylates.

Examples of tri and or higher (meth)acryloyl esters crosslinking agents include trimethylol propane tri(meth)acrylate, ethoxylated glycerin tri(meth)acrylate, ethoxylated trimethylolpropane tri(meth)acrylate, ditrimethylol propane tetra(meth)acrylate, pentaerythritol tri(meth)acrylate, pentaerythritol tetra(meth)acrylate, propoxylated pentaerythritol tetra(meth)acrylate, ethoxylated pentaerythritol tetra(meth)acrylate, dipentaerythritol penta(meth)acrylate, dipentaerythritol hexa(meth)acrylate, and ethoxlated iscyanuric acid tri(meth)acrylates.

In some embodiments the (meth)acrylate monomer or oligomer can be the reaction product of the core polyol, the (meth)acrylate monomer, and one or more co-reactants selected from the group consisting of an organic diisocyanate, a polyacid, a polyester, a cyclic lactone, a cyclic lactam, an ethylene oxide, a propylene oxide, an epoxy compound, a polyol, and a polyamine.

Examples or organic diisocyanate co-reactants are toluene diisocyante, methylene diphenyl, diisocyanate, isophorone diisocyanate, and hexamethylene diisocyanate Examples of suitable polyacids and polyesters are malonic acid, succinic acid, glutaric acid, adipic acid, pimelic acid, suberic acid, azelaic acid, sebacic acid, terepthalic acid, isophthalic acid, and ortho-phthalic acid and their C1-C12 esters.

Examples of cyclic lactams are butyro, valero, and caprolactam.

Examples of cyclic lactones are butyro, valero, and caprolactone

An example of an epoxy compound is bisphenol A epoxy.

The (meth)acrylate monomer or oligomer can be crosslinked by exposure to UV or daylight radiation, as is conventional in this art. In some embodiments the composition further comprises an ethylenically unsaturated crosslinking monomer. The preferred cross-linking monomers are (meth)acrylate crosslinking monomers. The composition can include other monomers, oligomers, and/or polymers which are ethylenically unsaturated and which react in the presence of radiation.

The photopolymerizable (meth)acrylate monomers and oligomers can be, in some embodiments, the reaction product of the core polyol, a (meth)acrylate monomer, and one or more co-reactants selected from the group consisting of an organic diisocyanate, a polyacid, polyester, cyclic lactone, cyclic lactam, ethylene oxide, propylene oxide, an epoxy compound, polyols and polyamines and the composition further includes an ethylenically unsaturated (meth)acrylate crosslinking monomer.

The photopolymerizable monomers or oligomers can be urethanes based on aliphatic, aromatic, polyester, and polyether polyols as well as the core polyol, and aliphatic, aromatic, polyester, and polyether diisocyanates capped with (meth)acrylate end-groups. Isocyanate prepolymers can also be used in place of the polyol-diisocyanate core. Epoxy (meth)acrylates and epoxy urethane (meth)acrylates which have at least two or more acryl or methacryl groups and, optionally, a urethane group can be used, for example epoxy (meth)acrylates based on aliphatic or aromatic epoxy prepolymers capped with (meth)acrylate end-groups. An aliphatic or aromatic urethane spacer can be optionally inserted between the epoxy and the (meth)acrylate end group(s). Acrylated polyester oligomers, useful in the present invention, have at least two or more acryl or methacryl groups and a polyester core. Suitable acrylated polyether oligomers have at least two or more acryl or methacryl groups and a polyether core. Suitable acrylated acrylate oligomers have at least two or more acryl or methacryl groups and a polyacrylic core. These reactive urethanes, epoxies, polyesters, polyethers and acrylics are available from several suppliers including, for example, BASF Corporation, Bayer MaterialScience, Bomar Specialties Co, Cognis Corporation, Cytec Industries Inc, DSM NeoResins, Eternal Chemical Co, Ltd, IGM Resins, Rahn AG, Sartomer USA, LLC, and SI Group, Inc.

Combinations of two or more materials containing free radical polymerizable groups may be used in combination.

Examples of suitable photoinitiators are benzyl ketones, monomeric hydroxyl ketones, polymeric hydroxyl ketones, alpha-amino ketones, acyl phosphine oxides, metallocenes, benzophenone, benzophenone derivatives, and the like. Specific examples include: 1-hydroxy-cyclohexylphenylketone, benzophenone, 2-benzyl-2-(dimethylamino)-1-(4-(4-morphorlinyl)phenyl)-1-butanone, 2-methyl-1-(4-methylthio)phenyl-2-(4-morphorlinyl)-1-propanone, diphenyl-(2,4,6-trimethylbenzoyl) phosphine oxide, phenyl bis(2,4,6-trimethylbenzoyl) phosphine oxide, benzyl-dimethylketal, isopropylthioxanthone, and mixtures thereof.

Photo accelerators such as aliphatic or aromatic amines may also be included in the gel as well as fillers, inhibitors, plasticizers and adhesion promoters.

Suitable colorants which can be incorporated into the color concentrates include barium, calcium and aluminum lakes, iron oxides, chromates, molybdates, cadmiums, metallic or mixed metallic oxides, talcs, carmine, titanium dioxide, chromium hydroxides, ferric ferrocyanide, ultramarines, titanium dioxide coated mica platelets, and/or bismuth oxychlorides, Preferred pigments include D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, as well as others listed on the FDA color additives website, and Annex IV of the Cosmetic Directive 76/768/EEC, Coloring Agents Permitted in Cosmetics as of Mar. 1, 2010.

Pigment levels in the composition can be from greater than 0.1-wt % up to as much as 20-wt %. Colored pigments are preferred from 0.5 up to 10-wt %. Mixtures of TiO2 and colored pigments are most preferred.

Preferably the compositions comprise a colorant which is conventional in photocurable nail coatings.

The core polyol derived from a renewable resource is a naturally occurring renewable compound which contains pendant hydroxyl groups. Examples of core polyols are sucrose, soy, resorcinol, sorbitol, glucose, monosaccharides, disaccharides, oligosaccharides, and polysaccharides.

Upon exposure to actinic radiation the photopolymerizable composition polymerizes to form a hard and solvent resistant coating on the nails. In some embodiments the core polyol contributes to improved adhesion, application performance, wear, and/or durability of photopolymerized nail coatings.

The core polyol is preferably sucrose, soy, resorcinol, sorbitol, glucose, or a different naturally occurring monosaccharide, disaccharide, oligosaccharide, or polysaccharide.

The coating compositions can contain solvents, pigments, modifying resins, plasticizers, and other compounds mixed and maintained in a liquid solution.

EXAMPLES

The following examples illustrate a few non-limiting embodiments of the invention.

Example 1

Compositions shown in Table 1 were made up and cured for 3 min under standard UV lights used for curing nail gels. All compositions gave good cure properties, good flexibility and were suitable for use as cosmetic coatings for natural and artificial nails of humans and animals.

TABLE 1

| Component[1] | Example 1 | Example 2 | Example 3 | Example 4 | Example 5 |
|---|---|---|---|---|---|
| Sucrose based polymethacrylated monomer[1] | 37.3% | 56.1% | | | 32.0% |
| Photoinitiator[2] | 1.0% | 1.4% | 1.6% | 2.0% | 1.0% |
| Aliphatic polyurethane acrylate | 61.8% | 42.5% | 50.7% | 30.9% | 67.0% |
| D&C Violet 2 | 0.001% | 0.001% | 0.002% | 0.002% | 0.039% |
| Sefose based polymethacrylated monomer[3] | | | 44.3% | 63.7% | |
| Hydroxypropyl methacrylate | | | 3.4% | 3.5% | |

[1]NTX11475 = from Sartomer, Inc.
[2]Dar 4265 = Darocure 4265 from BASF Resins
[3]NTX11467 = from Sartomer, Inc. "Sefose" is a brand of sucrose polyester with an average degree of esterification of at least 7.7 of the 8 total hydroxyls The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A cosmetic coating formed on a antural or artificial fingernail or toenail by exposigin a photopolymerizable composition comprising a photoinitiator and a (meth)acrylate monomer or oligomer prepared by reacting a sucrose or resorcinol core polyol with a (meth)acrylate monomer to light.

2. The cosmetic coating of claim 1 wherein the (meth)acrylate monomer or oligomer is the reaction product of the core polyol, the (meth)acrylate monomer, and one or more co-reactants selected from the group consisting of an organic diisocyanate, a polyacid, polyester, cyclic lactone, cyclic lactam, ethylene oxide, propylene oxide, an epoxy compound, a polyol, and a polyamine.

3. The cosmetic coating of claim 1 further including an ethylenically unsaturated crosslinking monomer not derived from a core polyol.

4. The cosmetic coating of claim 1 further including a (meth)acrylate crosslinking monomer.

5. The cosmetic coating of claim 1 wherein the (meth)acrylate monomer or oligomer is the reaction product of the core polyol, the (meth)acrylate monomer, and one or more co-reactants selected from the group consisting of an organic diisocyanate, a polyacid, polyester, cyclic lactone, cyclic lactam, ethylene oxide, propylene oxide, and an epoxy compound, and the composition further includes an ethylenically unsaturated (meth)acrylate crosslinking monomer.

6. The cosmetic coating of claim 1 whereby formulated so that upon exposure to actinic radiation said photopolymerizable composition polymerizes to form a hard and solvent resistant coating on said nails.

7. The cosmetic coating of claim 1 wherein the core polyol contributes to improved application performance, adhesion, wear, and/or durability of photopolymerized nail coatings.

8. The cosmetic coating of claim 1 further including one or more additives selected from the group consisting of pigments, colorants, dyes, UV absorbing or reflecting materials, micas, glitters, flavors, and fragrances.

9. The cosmetic coating of claim 1 further including a methacrylate monomer which is not derived from a core polyol.

10. The cosmetic coating of claim 1 further including a methacrylate-containing oligomer which is not derived from a core polyol.

11. A photopolymzeriable composition for forming a cosmetic coating for natural and artificial nails of humans and animals comprising a photoinitiator and a (meth)acrylate monomer or oligomer prepared by reacting a sucrose core polyol with a (meth)acrylate monomer.

* * * * *